(12) United States Patent
Guo

(10) Patent No.: US 11,472,851 B2
(45) Date of Patent: Oct. 18, 2022

(54) RECOMBINANT BACILLUS SUBTILIS AND APPLICATION THEREOF

(71) Applicant: Huzhou Jiuyuan Bio-tech Co, Ltd., Huzhou (CN)

(72) Inventor: Liangxing Guo, Huzhou (CN)

(73) Assignee: HUZHOU JIUYUAN BIO-TECH CO, LTD., Huzhou (CN)

( * ) Notice: Subject to any disclaimer, the term of this patent is extended or adjusted under 35 U.S.C. 154(b) by 1 day.

(21) Appl. No.: 16/998,607

(22) Filed: Aug. 20, 2020

(65) Prior Publication Data

US 2021/0163548 A1    Jun. 3, 2021

(30) Foreign Application Priority Data

Dec. 2, 2019  (CN) .......................... 201911218140.5

(51) Int. Cl.
  *C07K 14/32* (2006.01)
  *C12N 15/75* (2006.01)

(52) U.S. Cl.
  CPC .............. *C07K 14/32* (2013.01); *C12N 15/75* (2013.01)

(58) Field of Classification Search
  None
  See application file for complete search history.

(56) References Cited

FOREIGN PATENT DOCUMENTS

CN    112029697 A    12/2020

OTHER PUBLICATIONS

Office Action with English translation for corresponding Chinese patent application No. CN201911218140.5, dated Apr. 21, 2021, 8 pp.

*Primary Examiner* — Suzanne M Noakes
(74) *Attorney, Agent, or Firm* — The Roy Gross Law Firm, LLC; Roy Gross

(57) ABSTRACT

The present invention provides a recombinant *Bacillus subtilis* JY011802 that can produce sublancin in a high yield, which was deposited at the China General Microbiological Culture Collection Center on Oct. 31, 2018 with an accession number of CGMCC No. 16667, and an application thereof. The yield of the sublancin produced by the recombinant *Bacillus subtilis* can reach 3100 mg/L.

5 Claims, 5 Drawing Sheets

Specification includes a Sequence Listing.

RECOMBINANT BACILLUS SUBTILIS AND APPLICATION THEREOF

REFERENCE TO AN ELECTRONIC SEQUENCE LISTING

The contents of the electronic sequence listing created on 12.2.2019 named sequence listing.txt and 7215 bytes in size, is hereby incorporated by reference in its entirety.

TECHNICAL FIELD OF THE INVENTION

The invention belongs to the field of microorganisms, in particular, the invention relates to a recombinant *Bacillus subtilis* and its application in the production of sublancin.

BACKGROUND OF THE INVENTION

The problem of bacterial resistance caused by overuse of antibiotics has become increasingly prominent, making clinical anti-infective treatment in a difficult situation. In the breeding industry, the long-term use of antibiotic growth promoters is even more serious. Not only does a large amount of antibiotic residues indirectly harm human health, but it also causes low immunity of livestock and poultry, increases the incidence of infectious diseases, and increases the cost of breeding. At present, diseases caused by bacteria, viruses, parasites, etc. are still important factors restricting large-scale farming. With the development of modern veterinary medicine, immunology and molecular biology, it has been found that the occurrence and development of many livestock and poultry diseases are closely related to the body's low immune function. The treatment direction has been adjusted from directly killing or inhibiting pathogenic bacteria to improving the body's immunity. Immune modulators can promote humoral immunity and cellular immunity of the body, with high safety and without any drug residue.

Antimicrobial peptides (AMPs) are the oldest antimicrobial infection peptides in biological evolution. They are an important part of innate immune regulation of various organisms from prokaryotes to humans. They are inherent immune effector molecule having direct effect of antimicrobial and bacterial flora regulation. In history, the antimicrobial function of antimicrobial peptides was first recognized, so it was first named antimicrobial peptides. With the gradual and deep understanding of the structure and function of these substances, antimicrobial peptides have been found to play a very important role in regulating the body's immune response in recent years. Many antimicrobial peptides are a bridge between innate immunity and acquired immunity. Antimicrobial peptides exert their anti-infective effects through direct microbicidal/microbial inhibition effects and increase in the level of the body's immune response. This is why antimicrobial peptides are superior to antibiotics. Therefore, now antimicrobial peptides are also called immune defense peptides.

Current research shows that antimicrobial peptides have broad-spectrum antibacterial, antiviral, antitumor and antiprotozoal activities, and can regulate body immunity, and are not prone to drug resistance. Antimicrobial peptides have a variety of immune regulatory effects, including regulating inflammatory responses, chemotaxis of immune cells, promoting cell differentiation, activating the innate and acquired immune systems, and so on. The various immunomodulatory properties of antimicrobial peptides make them promising drugs for treating infectious and immune diseases.

Sublancin obtained by fermentation, isolation and purification of *Bacillus subtilis* modified by genetic engineering means is a kind of antimicrobial peptide. Pharmacological experiments show that Sublancin can enhance the phagocytosis of macrophages. Clinical trials have shown that Sublancin can enhance the immune function of poultry, improve the immune effect of vaccines, and has high safety without any drug residue.

There are also some studies on Sublancin at home and abroad. In 1998, Paik S H et al. studied the chemical and biological structural characteristics and identification of transporter genes of the new lantibiotic Sublancin168 produced by *Bacillus subtilis* 168. It was concluded that Sublancin was a polypeptide composed of 37 amino acid residues, and contained two disulfide bonds. Its aqueous solution was stored at room temperature for two years without degradation and inactivation, which shows that it is relatively stable. Although Sublancin has a good potential to replace traditional antibiotics, the yield of Sublancin produced by *Bacillus subtilis* is very low and cannot meet the needs of large-scale use. Therefore, scholars at home and abroad have been working to improve the production of Sublancin. Shengyue Ji et al. improved the production of Sublancin by introducing three specific promoters to recombine the operon of *Bacillus subtilis*, and finally the yield of Sublancin produced by the recombinant *Bacillus subtilis* was increased to 642 mg/L fermentation broth. Recently, it has be shown from the latest research results of Northwest Agriculture and Forestry University in China that the optimization of fermentation parameters through chemometric methods and statistical experiment design will eventually increase the yield of Sublancin synthesized by *Bacillus subtilis* by 168 to 129.72 mg/L fermentation broth.

The structure of Sublancin has been systematically studied by scholars at home and abroad. Paik S H et al. used reverse HPLC method to confirm that the molecular weight of Sublancin was 3877.78 Da, and concluded that Sublancin 168 was a lantibiotic containing two disulfidebonds and composed of 37 amino acid residues by using N-terminal amino acid sequence analysis. Trent J. Oman et al. made further study by using tandem mass spectrometry to conclude that Sublancin 168 was not a lantibiotic, but a glycosylated polypeptide in which a glucose was linked to cysteine residue at position 22 and the molecular weight of this glucose is 162 Da. Recently, Garcia De Gonzalo C V et al. analyzed the tertiary structure of Sublancin through nuclear magnetic resonance (NMR) analysis. It can be seen from the results that Sublancin contains two alpha helixes, a clear inner helix loop region, and two disulfide bonds. These two alpha helixes contain the amino acid residues at positions 6-16 and the amino acid residues at positions 26-35 respectively. The inner helix loop region spans the amino acid residues at positions 17-25, and this inner helix loop region consisting of 9 amino acid residues also contains a β-S-glycosyl group linked to the cysteine at position 22. Hydrophobicity and hydrogen bonding ensure the stability of the loop structure, and this three-dimensional structure ensures the ultra-high stability of Sublancin.

SUMMARY OF THE INVENTION

The present inventors modified *Bacillus subtilis* by means of genetic engineering, and the yield of Sublancin produced by the modified *Bacillus subtilis* was greatly improved.

One object of the present invention is to provide a *Bacillus subtilis* with high yield of sublancin.

Another object of the present invention is to provide a method for producing a recombinant *Bacillus subtilis*.

Another object of the present invention is to provide a recombinant *Bacillus subtilis* obtained by the method for producing a recombinant *Bacillus subtilis*.

Another object of the present invention is to provide a method for producing sublancin.

In one aspect, the present invention provides a recombinant *Bacillus subtilis* JY011802 which was deposited on Oct. 31, 2018 at the China General Microbiological Culture Collection Center (referred to as CGMCC, address: Institute of Microbiology, Chinese Academy of Sciences, Building 3, No. 1, Beichen West Road, Chaoyang District, Beijing, Postcode 100101) under the Budapest Treaty with an accession number of CGMCC No. 16667.

In another aspect, the present invention provides a method for producing a recombinant *Bacillus subtilis*, the method comprises steps of:

1) ligating a target gene fragment expressing sublancin into a cloning vector (preferably pJET1.2/Blunt) to obtain a recombinant cloning vector, and then transforming the recombinant cloning vector into *Escherichia coli* (preferably BL21) for further cloning;

2) digesting the recombinant vector cloned in step 2 with endonuclease and then ligating the target gene into a pBS101 expression vector to obtain a recombinant plasmid;

3) transforming the obtained recombinant plasmid into a *Bacillus subtilis* 1A747 expression host by heat shock method, and collecting transformed *Bacillus subtilis* 1A747 cells;

4). Spreading the transformed *Bacillus subtilis* 1A747 bacterial cells on a LB medium plate and culturing until a single colony appears.

In another aspect, the present invention provides a recombinant *Bacillus subtilis* obtained by the above method.

In yet another aspect, the present invention provides a method for producing sublancin, wherein the above-mentioned recombinant *Bacillus subtilis* is used in the method.

In another aspect, the present invention provides a use of the aforementioned recombinant *Bacillus subtilis* JY011802 or the aforementioned recombinant *Bacillus subtilis* in fermentation production of sublancin.

Beneficial Effect

The yield of the sublancin produced by the recombinant *Bacillus subtilis* in the present application can reach 3100 mg/L, which is 20 times as much as the yield of the sublancin in the prior art. Therefore, by using it, the production efficiency of the sublancin can be greatly improved, and thus it has important economic value. In addition, the present inventors also carried out a comprehensive structural confirmation of the obtained Sublancin, and the results are consistent with those reported in domestic and foreign literatures. It has been indicated from the stability tests that Sublancin has strong stability and controllable quality.

DETAILED DESCRIPTION OF THE INVENTION

The following embodiments merely exemplarily illustrate specific modes of the present invention, and do not limit the scope of the present invention. The scope of the present invention is limited only by the attached claims and the equivalents thereof.

Preparation Example

Experimental Materials:
Templates and Strains
*Bacillus subtilis* 168 DNA template (NCBI reference sequence: NC_000964.3), *Escherichia coli* BL21 competent cells (Item No.: CD901-03, supplier: Beijing TransGen Biotechnology Co., Ltd.). *Bacillus subtilis* 1A747 (purchased from *Bacillus* Genetic Stock Centre of the Ohio State University (Columbus, Ohio, USA))

Figure 1:
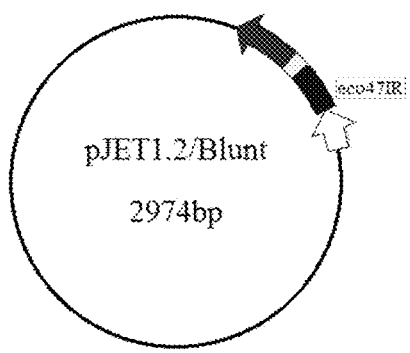
FIG. 1 shows the pJET1.2/Blunt cloning vector.
Figure 2:
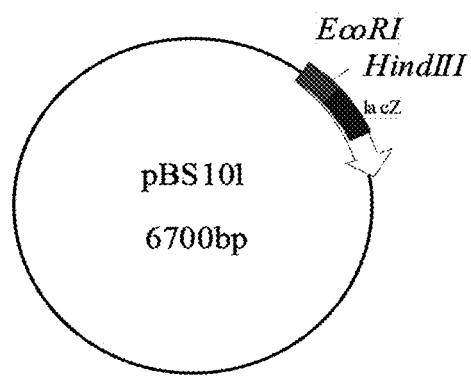
FIG. 2 shows the pBS101 expression vector.

Vectors:
The pJET1.2/Blunt cloning vector (FIG. 1) and pBS101 expression vector (FIG. 2) were products of Biovector.

1. PCR amplification of target gene fragment
The full sequence name of the target gene fragment was: sunI and sunA-sunT-bdbA-sunS-bdbB (SEQ ID No. 1).

Primer Premier software was used to design primers so that BamHI and SacII restriction sites were contained in both ends of the gene fragment product of interest, respectively.

2. Ligation of the target fragment into pJET1.2/Blunt vector and plasmid transformation 2.1 Ligation of the target fragment into pJET1.2/Blunt vector

TABLE 1.1

| Enzyme-linked reaction system | |
|---|---|
| ddH$_2$O | 13.5 μl |
| 10*T4 DNA Ligase Buffer | 2 μl |
| pJET1.2/Blunt vector | 0.5 μl |
| DNA | 3 μl |
| T4 DNA Ligase | 1 μl |
| Total | 20 μl |

The PCR product was well mixed with the above system, then the mixture was centrifuged briefly and left to stand at 16° C. overnight. The ligated system was stored in a refrigerator at 4° C. for later use.

2.2 Plasmid Transformation by Heat-Shock Method a. The prepared 100 μl of *Escherichia coli* BL21 competent cells were taken out from the freezer at −80° C. and were left on ice for 10 min to make them enter the 0° C. reception state. In a super clean bench, 10 μl of the corresponding enzyme-linked product was added to competent cells, the mixture was gently rotated and the contents were mixed well, and the mixture was placed on ice for 30 min (a control without plasmid DNA can be set in the test);

b. Heat shock: A thermometer was used to accurately adjust the temperature of the water bath to 42° C. The sample was taken out and immediately placed into a water bath at 42° C. for 90 s for accurate heat shock;

c. Icing: The EP tube was quickly removed and put into ice to cool the cells for 2 minutes;

d. Resuscitation: 400 μl of LB medium that has been pre-heated in an incubator at 37° C. was added to the EP tube and the EP tube was incubated with shaking in a shaker at 37° C. at 180 r/min for 1.5 h to recover the bacteria;

e. Spread plate: In the super clean bench, 300 μl and 150 μl of transformed competent cells were taken and transferred to a petri dish, respectively, and the transformed cells were spread uniformly on the surface of an agar plate with a sterile elbow glass rod;

f. Cultivation: The petri dishes were placed right side up in an incubator at 37° C. for cultivation until the liquid was absorbed, and then the petri dishes were inverted for cultivation. 12-16 hours later, colonies may appear.

g. MasterPlate: The petri dishes that have been cultured overnight were taken out. In the super clean bench, 10 single colonies from each petri dish were picked to 2 solid LB Petri dishes with a diameter of 15 cm and streaked for monoclonal expansion and further screening. The picked colonies were numbered 1-10 and cultured in an incubator at 37° C. for 12 hours.

3. Double digestion (BamHI and SacII) and ligation of plasmid and expression vector pBS101.

3.1 First the Mixture of the digestion system without the plasmid and the expression vector was prepared, and then each of the aliquots of Mixture was charged into 0.6 ml EP tube.

TABLE 1.2

| Endonuclease Digestion System | |
| --- | --- |
| ddH$_2$O | 30 μl |
| 10*Proteinase buffer | 4 μl |
| BamH I | 1 μl |
| SacII | 1 μl |
| plasmid | 4 μl |
| Total | 40 μl |

The endonuclease digestion was performed in an incubator at 37° C. for not more than 1.5 hours. 2 μl of 10× Buffer can be added to terminate the digestion. It was shown from the results that the digestion effect was good. The plasmid digested in the same step was used to recover the target fragment. The digested expression vector was first stored in a refrigerator at 4° C. for use.

3.2 Ligation of the recovered target fragment into the pBS101 expression vector

TABLE 1.3

| Enzyme-linked reaction system | |
| --- | --- |
| ddH$_2$O | 13.5 μl |
| 10*T4 DNA Ligase Buffer | 2 μl |
| pBS101 | 0.5 μl |
| DNA | 3 μl |
| T4 DNA Ligase | 1 μl |
| Total | 20 μl |

The components of reaction system were well mixed and centrifuged briefly. The prepared system was left to stand at 16° C. overnight. The ligated system was stored in a refrigerator at 4° C. for later use.

3.3 Plasmid transformation by heat shock method

The recombinant plasmid was transformed into a *Bacillus subtilis* 1A747 (purchased from *Bacillus* Genetic Stock Centre of the Ohio State University (Columbus, Ohio, USA)) expression host by a heat shock method, and the transformed *Bacillus subtilis* 1A747 cells were collected and spread on LB medium plate (10 g of tryptone, 5 g of yeast extract, 10 g of NaCl and 15 g of agar were dissolved in purified water and made up to 1 L with purified water). The cells were cultured at 37° C. until single colonies appear. After the transformants were correctly verified by plasmid extraction and PCR, the next cultivation and fermentation studies were performed.

Example 1 Cultivation of Recombinant *Bacillus Subtilis* Transformants 4 transformant single colonies and 1 *Bacillus subtilis* 1A747 single colony were picked and inoculated into 25 ml of liquid medium (30 g of corn flour, 18 g of soybean meal, 12.5 g of peptone, 15 g of glucose, 3 g of KH$_2$PO$_4$ and 1.25 g of ammonium sulfate were dissolved in purified water and made up to 1 L with purified water), respectively. They were cultured with shaking at 200 rpm for 12-18 hours at 37° C., and centrifuged at 10,000 rpm for 10 minutes. The supernatant was collected.

The concentration of the target polypeptide Sublancin in the supernatant was detected by high performance liquid chromatography.

The chromatographic conditions of high performance liquid chromatography were as follows:

Octylsilane-bonded silica gel was used as filler (High Performance Liquid Chromatograph: Agilent 1260, C8 chromatographic column: ZORBAX 300SB-C8, 5 m, 4.6×150 mm), and trifluoroacetic acid-water (1:1000) was used as mobile phase A, and trifluoroacetic acid-water-acetonitrile (0.85:200:800) was used as mobile phase B; column temperature was 25° C.; detection wavelength was 280 nm; flow rate was 1 ml/min; injection volume was 20 L; gradient elution was carried out according to the following Table 5. The number of theoretical plates was calculated to be not less than 2000 according to the Sublancin peak.

TABLE 2.1

| Elution gradients for HPLC | | |
| --- | --- | --- |
| Time (minutes) | A (%) | B (%) |
| 0 | 70 | 30 |
| 1 | 70 | 30 |
| 15 | 57 | 43 |
| 25 | 57 | 43 |
| 25.01 | 0 | 100 |
| 30 | 0 | 100 |
| 30.01 | 70 | 30 |
| 35 | 70 | 30 |

Figure 3:
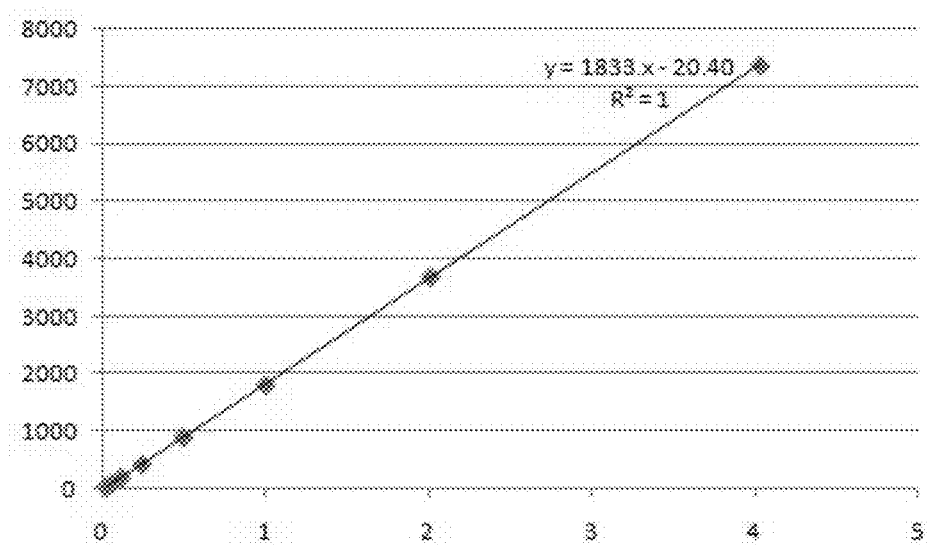
FIG. 3 is a standard curve of the peak area and concentration of the sublancin standard.

The peak position of the Sublancin standard was 8.5 min-10 min. The standard curve of the peak area and Sublancin concentration was shown in FIG. 3. The standard curve equation was y=1833.5x-20.405 (x was the standard concentration, the unit was mg/ml, and y was average peak area).

It was shown from the results that the concentrations of Sublancin in the supernatants obtained by the four transformed strains were 2980 mg/L, 2920 mg/L, 3010 mg/L, and 3100 mg/L, respectively, while the concentration of Sublancin in the supernatant obtained by *Bacillus subtilis* 1A747 was 100 mg/L. According to references[6,7], the current yields of Sublancin produced by *Bacillus subtilis* were 129 mg/L and 642 mg/L, respectively.

The strain with the highest yield of Sublancin (that is, the strain with a Sublancin concentration of 3100 mg/L in the supernatant) was named JY011802. *Bacillus subtilis* JY011802 has been deposited on Oct. 31, 2018 at the China General Microbiological Culture Collection Center (CGMCC, Address: Institute of Microbiology, Chinese Academy of Sciences, Building 3, No. 1, Beichen West Road, Chaoyang District, Beijing, Postcode 100101) with an accession number of CGMCC No. 16667.

Verification Examples

1. Mass Spectrometry

The Sublancin in the supernatant of strain JY011802 obtained in Example 1 was qualitatively analyzed by mass spectrometry, and the specific steps were as follows:

Name and model of test instrument: electrospray tandem mass spectrometer micrOTOF-Q II (Bruker), Agilent 1100 Series High Performance Liquid Chromatograph (HPLC, Agilent) Test sample: Sublancin The test results were shown in Table 3.1 below.

TABLE 3.1

Sublancin Comparison before and after reduction

| Sample | Molecular weight before reduction (Da) | Molecular weight after reduction (Da) | Molecular weight increment (Da) | Relative area increment (%) | Remarks |
|---|---|---|---|---|---|
| Sublancin | 3875.7292 | 3879.7669 | 4.0377 | 10.0 | Two pairs of disulfide bonds of component 1 were reduced |
| | 3713.6663 | 3717.6932 | 4.0269 | −9.0 | Two pairs of disulfide bonds of component 2 were reduced |
| | 7751.4231 | 7759.5087 | 8.0856 | −1.0 | Four pairs of disulfide bonds of component 3 were reduced |

Conclusion: LC-MTQ-MS was used to determine the exact molecular weight of Sublancin before and after reduction. It was shown from the results that the main component was the target molecule, whose complete molecular weight is 3875.7249D, and the relative deviation from the theoretical molecular weight (containing 2 pairs of disulfide bonds and 1 Hex modification) is less than 0.0004%. The measured molecular weight was consistent with the theoretical molecular weight. The molecular weight of the sample shown in the test result was basically the same as 3878.78 Da and 3875.75 Da of the molecular weights of Sublancin as reported in the References[1, 2, 3]. It can be seen that this sample had the structural information corresponding to Sublancin.

2. Amino Acid Sequence Determination

Name and model of detection instrument: Applied Biosystems 491 Protein Sequence Analyzer Test sample: Sublancin Test results:

(SEQ ID. No: 2)
H-Gly-Leu-Gly-Lys-Ala-Gln-Cys-Ala-Ala-Leu-Trp-Leu-

Gln-Cys-Ala-Ser-Gly-Gly-Thr-Ile-Gly-Cys-Gly-Gly-

Gly-Ala-Val-Ala-Cys-Gln-Asn-Tyr-Arg-Gln-Phe-Cys-

Arg-OH

The amino acid sequence of the sample shown in this test result was completely consistent with the amino acid sequence of Sublancin reported in References[1, 2, 3]. It can be seen that this sample had structural information corresponding to Sublancin.

3. Secondary Structure Detection

Name and model of detection instrument: circular dichroism spectrometer (model: JASCO J-810), Cell length=1 mm.

Test sample: Sublancin

Figure 4:
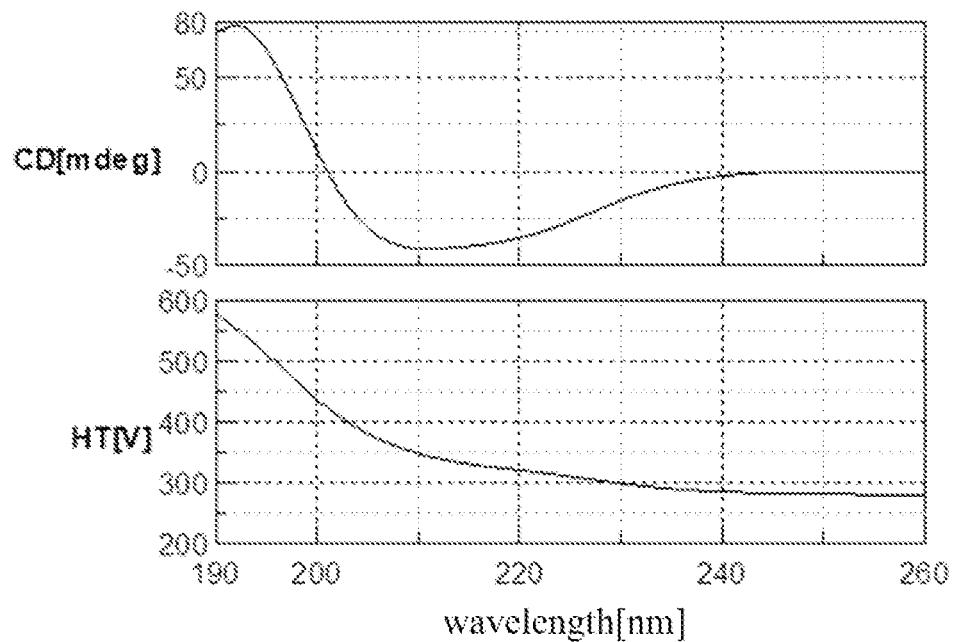
FIG. 4 shows the detection profile of the secondary structure of Sublancin detected by using circular dichroism spectrometer.

Test results: The test profile was shown in FIG. 4. The analysis results are shown in Table 3.2 below.

TABLE 3.2

| Structure | | fraction | ratio |
|---|---|---|---|
| English | Chinese | | |
| Helix | α-helix | 0.1 | 35.1% |
| Beta | β-sheet | 0.1 | 40.5% |

TABLE 3.2-continued

| Structure | | fraction | ratio |
|---|---|---|---|
| English | Chinese | | |
| Turn | β-turn angle | 0.0 | 0.0% |
| Random | Random coil | 0.1 | 24.4% |
| | Total | 0.3 | 100% |

4. Nuclear Magnetic Resonance (Tertiary Structure)

Name and model of test instrument: NMR spectrometer Agilent DD2 600 MHz

Test sample: Sublancin

Figure 5:
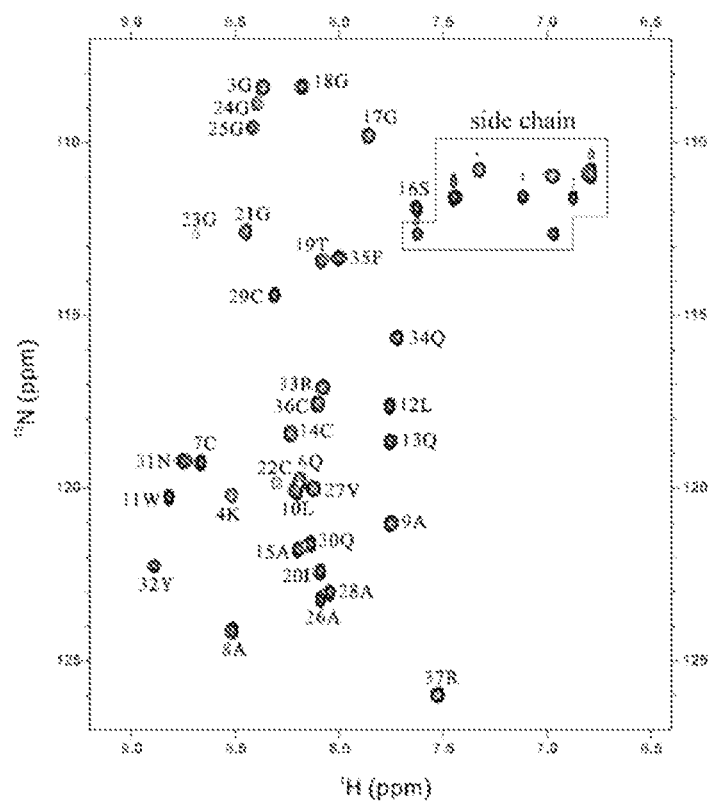
FIG. 5 shows the 1H-15N HSQC of the Sublancin sample.
Figure 6:
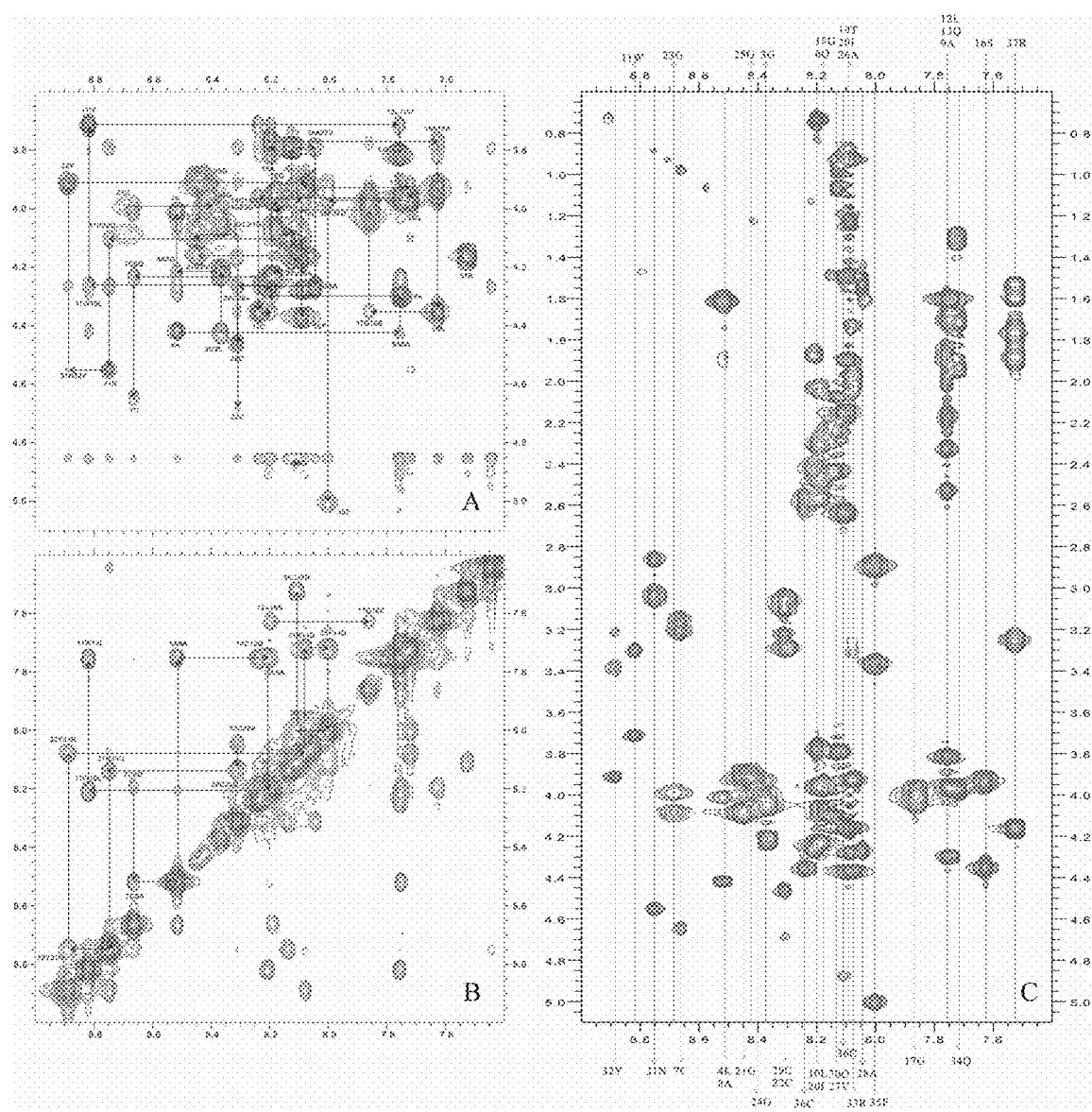
FIG. 6 shows the sequence connection relationship and spin system determination of Sublancin.

Test results: see FIG. 5, FIG. 6 and Table 3.3.

TABLE 3.3

Sublancin structure calculation statistics table

| | |
|---|---|
| Total number of structural calculation constraints | 562 |
| Total NOE Constraints | 508 |
| Within residue | 218 |
| Interresidue | 103 |
| Medium range | 75 |
| Remote | 68 |
| Multi-homing NOE | 44 |
| Dihedral angle constraint | |
| Φ angle | 30 |
| Ψ angle | 30 |
| Disulfide bonds C7—C36, C14—C29 | 2 |
| Hydrogen bond | 0 |
| Experimental constraint rmsd | |
| Bond length (Å) | 0.003 ± 0.000 |
| Bond angle (degrees) | 0.473 ± 0.016 |
| Discomfort torsion angle (degrees) | 1.626 ± 0.095 |
| Average pairwise rmsd | |
| Main chain: secondary structure region (Å) | 0.15 |
| Main chain: 1-37 residues (Å) | 0.86 |
| Heavy atom: secondary structure region (Å) | 0.63 |
| Heavy atom: 1-37 residues (Å) | 1.05 |
| Procheck analysis | |
| Optimum area (%) | 91.9 |
| Additional permitted area (%) | 8.1 |
| General allowed area (%) | 0 |
| Not allowed area (%) | 0 |

Figure 7:
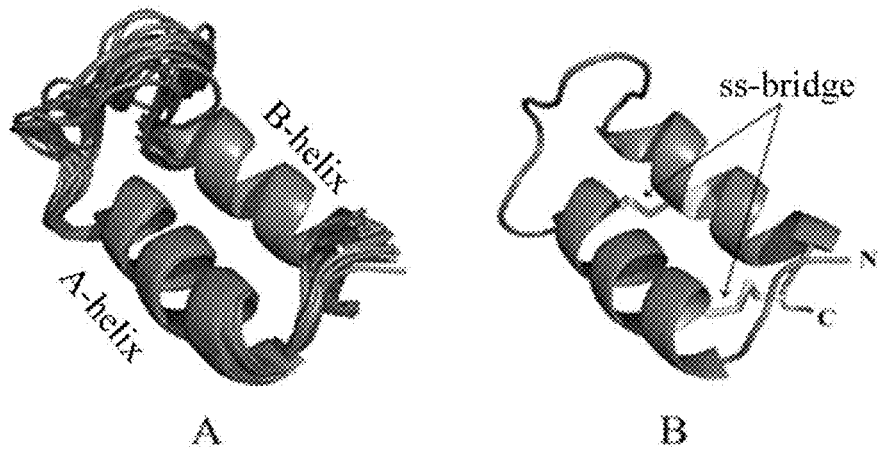
FIG. 7 is a schematic diagram of the three-dimensional structure of Sublancin.
Figure 9:
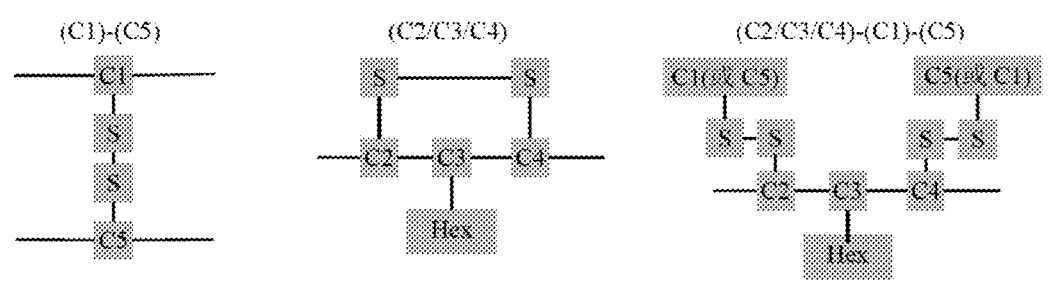
FIG. 9 is a schematic diagram of the disulfide bond connection of Sublancin.

Analysis: The calculated three-dimensional structure of the Sublancin sample was two nearly parallel α-helix structures connected by a central loop region (residues 16-24), where Helix A included residues 4-15 and Helix B included residues 25-35, the two helix structures were pulled closer to each other by two pairs of disulfide bonds (C7-C36, C14-C29) at the ends (FIGS. 7A and 7B). The 562 constraints were used for structure calculation (see Table 3.3), with an average of more than 15 constraints per residue. Without using hydrogen bonding constraints, a clear secondary structure region (residues 4-15 and residues 25-35) was obtained. Due to the constraints of the disulfide bond (C7-C36) at the end of the helix structure, a large number of NOE between L2-F35, and the non-secondary structure regions at the N and C terminals can be seen, and the structural calculation also converges well (FIG. 7A). There are fewer constraints in the central loop region, indicating greater flexibility in this region (FIG. 7A).

Glycan part only H1, Hβa, b of H1 and C22

Figure 8:
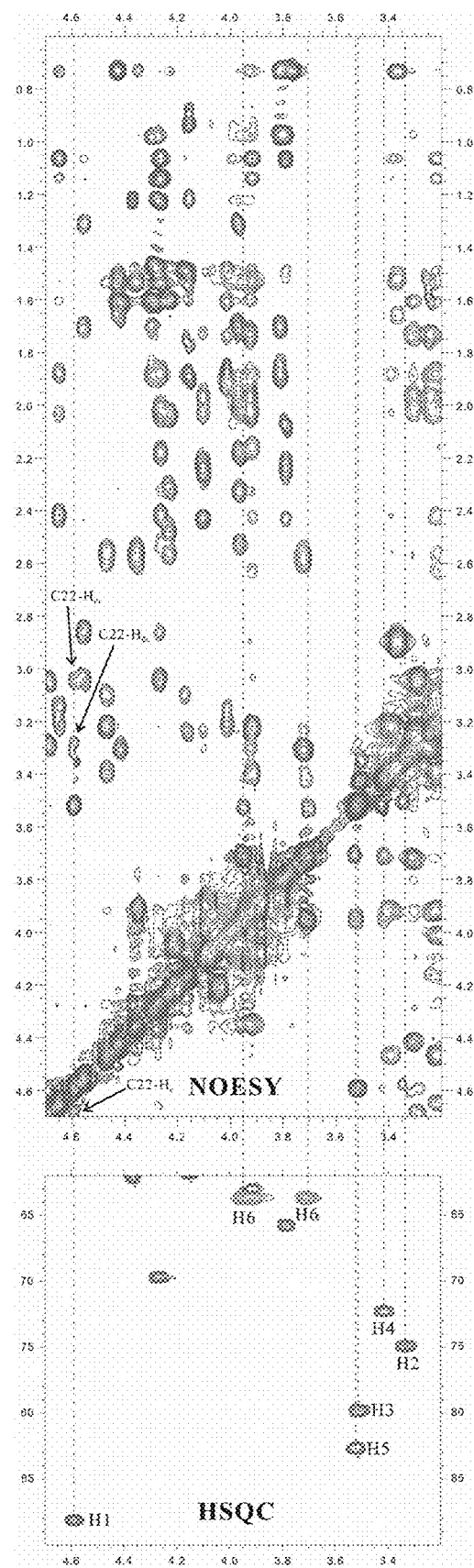
FIG. 8 shows the glycosyl moiety assignment and NOE information.

For the glycosyl moiety, only the NOE signals between $H_1$, C22 $H_\alpha$, $H_{\beta a,b}$ were shown (FIG. 8), indicating the position and the R configuration of the glycosyl linkage (if it was a configuration, there should also be a NOE signal between $H_2$ and C22 $H_\alpha$, $Hp_{\alpha,\beta}$). No other glycosyl signals and NOE information of the peptide other than the C22 residue were observed, indicating that the glycosyl moiety was a region with great flexibility, which had no definite relative positional relationship with the polypeptide moiety.

Conclusion: The NMR detection and analysis results of this sample were basically consistent with the Sublancin NMR detection and analysis results reported in References[4,5], and this sample had the structural information corresponding to Sublancin.

5. Infrared Absorption Spectrum

Name and model of detection instrument: VERTEX 70 Fourier transform infrared spectrometer (Bruker, German)

Test sample: Sublancin

Test results: see Table 3.4.

TABLE 3.4

Sublancin FT-IR characteristic peak analysis

| Peak Number # | Wave Number (cm−1) | Absorption Intensity | Type of Chemical Bond Vibration | Characteristics |
|---|---|---|---|---|
| 1 | 3300.1 | s | $v_{O-H}$, $v_{N-H}$ | Hydroxyl, peptide bond, amino |
| 2 | 3063.6 | m | $v_{Ar-H}$, $\delta_{N-H}$ octave peak | benzene ring, peptide bond |
| 3 | 2960.0 | m | $v_{-CH3}$ | alkyl |
| 4 | 2935.4 | m | $v_{-CH2}$ | alkyl |
| 5 | 2873.9 | m | $v_{-CH3}$ | alkyl |
| 6 | 1657.8 | s | $v_{C=O}$, amide I | peptide bond, α-helix |
| 7 | 1541.4 | s | $\delta_{N-H}$, $v_{C-N}$, $v_{C=C}$ | peptide bond, benzene ring |
| 8 | 1454.8 | m | $\delta_{-CH3}$ 和 $\delta_{-CH2}$ | alkyl |
| 9 | 1410.4 | m | $\delta_{-CH3}$ 和 $\delta_{-CH2}$ | alkyl |
| 10 | 1334.6 | m | $\gamma_{-CH2}$ | alkyl |
| 11 | 1299.4 | m | amide III | α-helix |
| 12 | 1242.9 | m | amide III | β-sheet |
| 13 | 1170.4 | m | $v_{C-O}$ | side chain hydroxyl |
| 14 | 1104.5 | w | $v_{C-O}$ | sugar, side chain hydroxyl |
| 15 | 1071.6 | w | $\gamma_{-CH}$, $v_{C-O}$ | alkyl, sugar |
| 16 | 1032.0 | w | $\delta_{-C-O}$ | silk amino acid side chain, sugar |
| 17 | 891.9 | w | $\delta_{-CH}$ | alkyl, sugar |
| 18 | 743.3 | w | $\delta_{=CH}$ | benzene ring |
| 19 | 612.9 | m | $v_{C=O}$, $v_{-SH}$ | carboxylic acid, amide conjugated system, disulfide bond |
| 20 | 551.4 | m | $v_{C=O}$, $v_{-SH}$ | carboxylic acid, amide conjugated system, disulfide bond |

Note:

v-stretching vibration, δ-bending vibration, γ-out-of-plane bending vibration, s-strong peak, m-medium strong peak, w-weak peak.

Analysis: Sublancin as the sample to be tested was tableted by using potassium bromide powder and then detected by using Fourier transform infrared spectroscopy. The wave number correlation coefficient was 1.00 (equivalent to 100% similarity). The molecular structure of the sample contained main structures such as amide I, amide III, amino, peptide bond, methyl, methylene, phenyl, glycosyl, disulfide bond, α-helix, β-sheet and the like.

Conclusion: In the infrared absorption spectrum of this sample, its absorption peak had the structural information corresponding to Sublancin, including main structural features such as amide I, amide III, amino, peptide bond, methyl, methylene, phenyl, glycosyl, disulfide bond, α-helix, ,β-sheet and the like, which were more obvious.

6. Confirmation of Sugar Structure

Name and model of detection instrument: Agilent 1100 Series High Performance

Liquid Chromatograph (HPLC, Agilent), micrOTOF-Q II Mass Spectrometer (Brook)

Test sample: Sublancin

Test results: see Table 3.5 and Table 3.6.

TABLE 3.5

Identification results of glycation modification sites

| Sample | Measured Molecular Weight (Da) | theoretical Molecular Weight (Da) | Characteristic sequence | Modification | Ion Score |
|---|---|---|---|---|---|
| Sublancin | 2204.8798 | 2204.9136 | LQCASGGTIGCGGGA VACQNY (SEQ ID. No: 3) | C14, C29: Carbamidomethyl (C); C22: Hex (C)* C22: Hex (C) | 484 |

Note*:
Hex was hexose (glucose), Reference[8].

TABLE 3.6

Results of saccharification rate at the SublancinCys22 site

| Category | Lot Number | Characteristic Ionic Strength* | Relative Strength (%) |
|---|---|---|---|
| Glycosylation Modification | Sublancin | 3671596 | 99.1 |
| Non-glycosylation Modification | Sublancin | 34420 | 0.9 |

Note*:
"$^{12}$LQCASGGTIGCGGGAVACQNY$^{32}$" (SEQ ID. No: 3) was selected as a reliable characteristic peptide based on the ion score and detection times.
CONCLUSION: The Sublancin as the sample to be tested was subjected to enzymatic hydrolysis and then reductive alkylation. It was detected by HPLC-MS/MS. It was shown from the results that all the glycation modification sites of the samples were at Cys22, the glycation rate was 99.1%, and the non-glycosylation modification rate was 0.9%.

The glycosylation modification sites shown in this test result were consistent with the conclusion that Sublancin had a glucose linked to the cysteine at position 22 reported in References[2, 4]. It can be seen that this sample had structural information corresponding to Sublancin.

7. Three-Dimensional Configuration of Disulfide Bonds

Name and model of detection instrument: Agilent 1110 HPLC, electrospray quadrupole time-of-flight tandem mass spectrometer (Q-TOF) micrOTOF-Q II Test sample: Sublancin Test results: see Table 3.7 and Table 3.8.

TABLE 3.7

Measured disulfide bond connection and detection frequency of Sublancin

| Disulfide Bond Connection | Sublancin | Notes |
|---|---|---|
| (C1)—(C5) | 17 | Expected disulfide bond |
| (C2/C3/C4) | 29 | Expected disulfide bond, including 1 Hex |
| (C2/C3/C4)—(C1)—(C5) | 3 | Unexpected disulfide bond, including 1 Hex |

TABLE 3.8

Relative strength and ratio of sublancin measured disulfide bond connection

| | Disulfide Bond Connection | 2016111601 | Notes |
|---|---|---|---|
| Strength | (C1)—(C5) | 560306 | Expected disulfide bond |
| | (C2/C3/C4) | 4096141 | Expected disulfide bond, including 1 Hex |
| | (C2/C3/C4)—(C1)—(C5) | 11091 | Unexpected disulfide bond, including 1 Hex |
| relative proportion (%) | Expected connection | 99.8 | |
| | Unexpected connection | 0.2 | |

Figure 10:
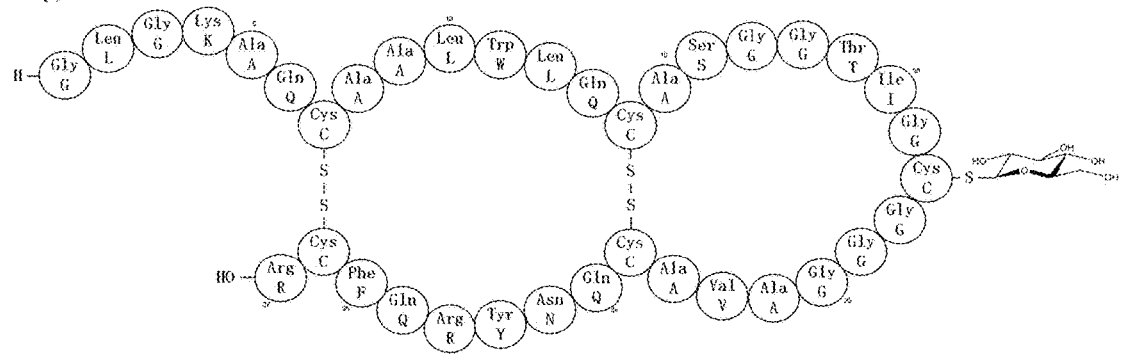
FIG. 10 shows the disulfide bond connection pattern of Sublancin (SEQ ID. No:2).

Conclusion: The samples were subjected to enzymolysis by using Chymotrypsin, and the comparison of samples was performed before and after reduction, and the samples were detected by using HPLC-MS/MS mass spectrometry. The main disulfide bond connection modes of Sublancin were obtained through analysis strategies such as "software comparison differences → data optimization and filtering → mother-child peptide verification → mass spectrum verification". The main disulfide bond connection modes were: (C1)—(C5), (C2)—(C4). Very few unexpected connections were also detected: (C2/C3/C4)—(C1)—(C5). See FIG. 10 for the connection mode. The disulfide bond connection sites shown in this test result were completely consistent with the Sublancin disulfide bond connection sites reported in the literatures[1, 2, 3, 4]. It can be seen that this sample had structural information corresponding to Sublancin.

REFERENCES

1. Paik S H, Chakicherla A, Hansen I N. 1998. Identification and characterization of the structural and transporter genes for, and the chemical and biological properties of, Sublancin 168, a novel lantibiotic produced by *Bacillus subtilis* 168 [J]. J Bio Chem. 273:23134~23142.
2. Oman, T. J., J. M. Boettcher, H. Wang, et al. 2011. Sublancin is not a lantibiotic but an S-linked glycopeptide [J]. Nat. Chem. Biol. 7:78~80.
3. Oman, T. J., J. M. Boettcher, H. Wang, et al. 2011. Supplementary Information for Sublancin is not a lantibiotic but an S-linked glycopeptide [J]. Nat. Chem. Biol. 7:S1~S78.
4. Garcia De Gonzalo C V, Zhu L, Oman T J, van der Donk W A 0.2014. NMR structure of the S-linked glycopeptide Sublancin 168 [J]. ACS Chemical Biology. 9:796~801.
5. Garcia De Gonzalo C V, Zhu L, Oman T J, van der Donk W A 0.2014. Supplementary Information for NMR structure of the S-linked glycopeptide Sublancin 168 [J]. ACS Chemical Biology. 9:S1~S16.
6. Shengyue Ji, Weili Li, Abdul Rasheed Baloch, Meng Wang, Binyun Cao. Improved production of sublancin via introduction of three characteristic promoters into operon clusters responsible for this novel distinct glycopeptide biosynthesis [J]. Microbial Cell Factories. 2015, 14: 17.
7. Shengyue Ji, Weili Li, Haiyun Xin, Shan Wang, Binyun Cao. Improved Production of Sublancin 168 Biosynthesized by *Bacillus subtilis* 168 Using Chemometric Methodology and Statistical Experimental Designs [J]. BioMed Research International. 2015, Article ID: 687915.
8. Oman T J, Boettcher J M, Wang H, et al. Sublancin is not a lantibiotic but an S-linked glycopeptide[J]. Nature Chemical Biology, 2011, 7(2):78.

---

The invention claimed is:

1. A recombinant *Bacillus subtilis* JY011802 which was deposited at the China General Microbiological Culture Collection Center on Oct. 31, 2018 with an accession number of CGMCC No. 16667.

2. A method for producing a recombinant *Bacillus subtilis*, the method comprises steps of:
   1) ligating a target gene fragment expressing sublancin into a cloning vector to obtain a recombinant cloning vector, and then transforming the recombinant cloning vector into *Escherichia coli* for further cloning;
   2) digesting the recombinant cloning vector cloned in step 1) with endonuclease, and then ligating the target gene into a pBS101 expression vector to obtain a recombinant plasmid;
   3) transforming the obtained recombinant plasmid into a *Bacillus subtilis* 1A747 expression host by heat shock method, and collecting transformed *Bacillus subtilis* 1A747 cells; and
   4) Spreading the transformed *Bacillus subtilis* 1A747 cells on a LB medium plate and culturing until a single colony appears, thereby producing the recombinant *Bacillus subtilis*.

3. A recombinant *Bacillus subtilis* obtained by the method of claim 2.

4. A method for producing sublancin, comprising cultivating the recombinant *Bacillus subtilis* JY011802 according to claim 1 in a fermentation medium in order to produce said sublancin.

5. A method for producing sublancin, comprising cultivating the recombinant *Bacillus subtilis* JY011802 according to claim 2 in a fermentation medium in order to produce said sublancin.

* * * * *

SEQUENCE LISTING

```
<160> NUMBER OF SEQ ID NOS: 3

<210> SEQ ID NO 1
<211> LENGTH: 4728
<212> TYPE: DNA
<213> ORGANISM: Artificial Sequence
<220> FEATURE:
<223> OTHER INFORMATION: target gene

<400> SEQUENCE: 1
atggaatatg tagttatgat aatcatttta ttagcacttt tctttatttt tactgttttc     60
ctaaatacac gttatagttt tgatgaaaaa tgcttagtct taaaatttgg tttatctaaa    120
acagaaattc aattaatca aatagttagt attaaagagt cagacaagta tggagttgca     180
gataatatcg attataaaat tggtatgcca tatgctcaac cagatagaat tgttattgaa    240
actacaaata agcgttttct agttttttta aatggagctc aacaatttat tcaaaagtat    300
aaaagggtta gtgtttgaat ggaaaagcta tttaagaag ttaaactaga ggaactcgaa     360
aaccaaaaag gtagtggatt aggaaaagct cagtgtgctg cgttgtggct acaatgtgct    420
agtggcggta caattggttg tggtggcgga gctgttgctt gtcaaaacta tcgtcaattc    480
tgcagataat tgaataagaa aaagaaatat gttcatacta aacagtttaa tagtcatgat    540
tgtggactag cttgtatctc gtcaattta aagtttcata accttaacta tggaattgat    600
ttcttactag acctaattgg ggataaggaa ggctatagtt taagagactt aattgttatt    660
tttaagaaga tggggataaa aactaggcca cttgaattgc aagaaaataa gacattcgaa    720
gccctaaaac aaataaagct cccttgtata gctttgttag aaggggagga atatggacat    780
tacataacaa tatacgaaat tagaaataac tatttacttg ttagtgatcc tgataaagac    840
aaaataacta aaataaaaaa agaggatttt gaaagtaaat tcacaaactt tatattgaaa    900
attgacaaag agtcaattcc tgaaaagaa aagatcaaa aaaacattc ttactttttt      960 aaggacatac tttttagaaa taattgatc gttttgtga ttttattgac ttccttgttc    1020
gttgtgggtc ttgctgtagc tgggtcgttt tatataaagt ttctagttga cctaattatc    1080
ccaagaagct taagagaatc tttaatcaca atcactttaa tattcataag tatggtctta    1140
ataaggtgca tcttcgattt tgtaagatca tatttgataa taaaattgtc ttacaaagtt    1200
gataaagaga tgtcaaatgt ttatttttaat aaagtaacaa aattacctat taattttttt   1260
gaaaacagag aagatggaga ggtaatttct cgattcaatg atggtatata tattaaagac  1320
```

```
tttttttagtg ctaactttgt tactgcaata attgatataa ttttaatact gggattagga      1380
gttattttat atagaacaaa taacattctt ttcttaacaa ttattctccc gattttgcta      1440
ctttcatgtc tagcgatttt gttttttgat catcttaaaa agaaaaatca aaaactgatg      1500
gaggataagg ctaaatctac ctctcttttta attaattttc tgaagaatat gacaactgtt      1560
tattctttaa ataaaacctc gttttttttta gaaaaatttc atcttacata tgataaacaa      1620
ttaaattcaa cctttagtgt agcaaaggca gttattagca atgaaatact aaaaggatta      1680
attcaaaact cttttacaat aattatccta tgggttggga caagacaagt tctaaatgat      1740
tcaatgagtt tgggtacact gctatttata aacacattag cagccttttt gctaagttca      1800
ctagatcgta tattgagtat gcaatcagat cttcagcagg cacatgttgc ttccataaga      1860
tttttttgacg tagtaaacta tccagttcag caagatagca atgagaattt aactgaactt      1920
gattttattc agaatatcaa aacagttaat cttaatattg gggcagaccc aatgcgttat      1980
atagttgaag atattaattt aatattagac agaaaggata agtcctttat tattggagaa      2040
agtggtactg gaaaaagtac gtttgcaaaa agtttgtcta aattgtataa agtacccgat      2100
aagtcaattt atttaaatgg attagatatt aatcgatacg atcatttatc aataagaaaa      2160
aggattgtat atattgacga aaatcctttt cttttttaagg gaaccattaa agagaatctt      2220
tgcatgggag agatttttga tcagaacgaa attgaaaacg cgtgtataat gtcccaatgc      2280
catgaattca tttgtaactt ggacaagcag tacagttata aattgtctga aaacggttcc      2340
aatctatcta caggacaaaa acaacggtta gcattagcaa gagcaattttt acatcaacca      2400
caagtattaa ttttagatga gtcattatct aacattgatc cggataacac aaaattgatt      2460
tatgaaacct tacacaggat ggattgttta attattctta taactcataa tgacccaagt      2520
aacttcaaat acaataaaaa attagtattc agaaacaata ggattataga gtcgagctac      2580
tcggaaaata aggagtattc tatatgaaaa agtggattgt tttatttctt gttttaatag      2640
cagcagccat tagtattttc gtttatgttt ctacaggtag cgaaaaacct ttttataatg      2700
atataaattt aactcaatat caaaaagaag tagactctaa aaaacctaaa tttatttatg      2760
tttatgagac aagttgtcct ccttgtcaag aaataaaacc tgagttaaat gaagtaatta      2820
aaaaagaaaa gttaaaagta caggctttaa atattgaaga aaaggaaaat tataacactg      2880
aattttttaga taaatataat ttgaataaaa ctccaacgat tctctattac aaagatggca      2940
aagaaaaaga tcggttagag ggctatagaa gtgcaagcca aatagaaaag ttctttgata      3000
aaaatggtga tagataatga aactgagtga tatttatttg gaattaaaga aaggctatgc      3060
cgattcttta ttgtattcag atttgtcatt gttggttaat ataatggaat atgaaaaga      3120
tattgatgtg atgtcaattc aatctttggt tgcaggttat gaaaaatcag atactcctac      3180
aataacatgc ggtattatag tttataacga aagcaagaga attaaaaagt gtttaaatag      3240
tgttaaagat gattttaacg agattattgt tctagattca tactccactg atgataccgt      3300
tgatattatt aaatgtgatt ttcctgatgt tgaaattaaa tatgaaaagt ggaagaatga      3360
ttttttcctat gctagaaata aaattataga gtatgctact tccgaatgga tttatttat       3420
tgatgcagat aatttatact ctaaagaaaa caagggaaaa atagctaaag tagctagagt      3480
tttagagttt ttttctattg attgtgtagt tagtccatat atagaagaat atactggaca      3540
tctatattct gatacacgaa gaatgtttcg gctcaatggt aaagttaaat tcatgggaa      3600
agtgcatgaa gaacctatga attataatca tagtctacct tttaatttca ttgtgaacct      3660
taaggtttac cataatggat ataatccttc agagaataat ataaaatcaa aaacacgaag      3720
```

```
gaatataaat ctcacagaag aaatgttaag attggagccc gaaaacccaa aatggttatt      3780 cttttcggc agagaactac atttacttga taaagatgaa gaagcaattg attatctgaa       3840
aaaatcaata aacaactata aaaaatttaa tgatcaaaga cattttatag atgctttagt      3900
gctattatgt actttattat tgcagagaaa taattatgtt gacttaactt tatatttgga      3960
tatattggaa actgaatatc caagatgtgt tgatgttgat tactttagat ctgcaatttt      4020
gttagtagat atgcaaaata aacttacttc tttaagcaat atgattgatg aagctcttac      4080
agacgagaga tacagtgcta taaatacaac aaaagatcac tttaaaagaa ttttaataag      4140
ccttaatatt caactcgaaa attgggaaag agtaaaagaa atatcagggg aaattaaaaa      4200
tgataatatg aaaaaagaaa ttaaacaata tcttgccaac tcactccaca atattgaaca      4260
cgtcctgaaa ggaattgaag tatgaataca agatatgtaa aatcattttt tttattactg      4320
ttttttctct ctttctttgg cacaatggct agtttattct acagtgagat catgcatttc      4380
aaaccatgtg ttctatgttg gtatcaaaga atatttctat atcctatacc tattatctta      4440
ctaataggct tattaaaaaa agatcttaat tcgatatttt atgttgtttt cctttcatca      4500
attggattga ttattgcgtt ttatcattat attatccaac ttacacaaag caaaagtgtc      4560
gtatgtgaaa ttggaaccaa cagctgcgca aaaattgaag tagagtatct aggctttatt      4620
acattaccct taatgagttc agtatgtttt gcattgatat ttggtatagg actgaaatta      4680
attatcaaaa gcaagaaatt aaaacaaaat caacatgtat ataattga                  4728

<210> SEQ ID NO 2
<211> LENGTH: 37
<212> TYPE: PRT
<213> ORGANISM: Artificial Sequence
<220> FEATURE:
<223> OTHER INFORMATION: Sublancin

<400> SEQUENCE: 2

Gly Leu Gly Lys Ala Gln Cys Ala Ala Leu Trp Leu Gln Cys Ala Ser
1               5                   10                  15

Gly Gly Thr Ile Gly Cys Gly Gly Gly Ala Val Ala Cys Gln Asn Tyr
            20                  25                  30

Arg Gln Phe Cys Arg
        35

<210> SEQ ID NO 3
<211> LENGTH: 21
<212> TYPE: PRT
<213> ORGANISM: Artificial Sequence
<220> FEATURE:
<223> OTHER INFORMATION: fragment of Sublancin

<400> SEQUENCE: 3

Leu Gln Cys Ala Ser Gly Gly Thr Ile Gly Cys Gly Gly Gly Ala Val
1               5                   10                  15

Ala Cys Gln Asn Tyr
            20
```